United States Patent [19]

Vocal

[11] Patent Number: 4,812,305

[45] Date of Patent: Mar. 14, 1989

[54] WELL MEDICINE STRIP

[76] Inventor: Rodolfo S. Vocal, P.O. Box 637, Mansfield, Ohio 44901-0637

[21] Appl. No.: 118,609

[22] Filed: Nov. 9, 1987

[51] Int. Cl.[4] ............................................. A61F 13/02
[52] U.S. Cl. .................................... 424/448; 424/449
[58] Field of Search ............................... 424/448, 449

[56] References Cited

U.S. PATENT DOCUMENTS

| | | | |
|---|---|---|---|
| 2,235,436 | 3/1941 | Laub | 128/2 |
| 2,561,071 | 7/1951 | Prisk | 128/260 |
| 3,598,122 | 8/1971 | Zaffaroni | 424/448 |
| 3,598,123 | 8/1971 | Zaffaroni | 424/448 |
| 3,699,963 | 10/1972 | Zaffaroni | 128/268 |
| 3,797,494 | 3/1974 | Zaffaroni | 424/448 |
| 4,060,084 | 11/1977 | Chandrasekaran et al. | 128/260 |
| 4,117,841 | 10/1978 | Perrotta et al. | 424/448 |
| 4,286,592 | 9/1981 | Chandrasekaran et al. | 128/260 |
| 4,297,995 | 11/1981 | Golub | 128/156 |
| 4,323,557 | 4/1982 | Rosso et al. | 424/448 |
| 4,341,208 | 7/1982 | Gordon | 128/156 |
| 4,402,696 | 9/1983 | Gulko | 424/449 |
| 4,421,737 | 12/1983 | Ito et al. | 424/448 |
| 4,460,368 | 7/1984 | Allison et al. | 424/449 |
| 4,486,194 | 12/1984 | Ferrara | 424/449 |
| 4,675,009 | 6/1987 | Hymes et al. | 424/449 |

Primary Examiner—Thurman K. Page
Assistant Examiner—L. R. Horne
Attorney, Agent, or Firm—Oldham & Oldham Co.

[57] ABSTRACT

An adhesive bandage having a well for receiving a medication supplied by the user and for confining the medication to a predetermined area. A flexible flap covers and seals the well.

10 Claims, 2 Drawing Sheets

WELL MEDICINE STRIP

BACKGROUND ART

1. Field of the Invention

The present invention relates to an adhesive bandage for confining medication to a predetermined area. More particularly, this invention relates to a novel adhesive bandage having a well for receiving a medication supplied by the user and for confining said medication to a predetermined area.

2. Description of the Related Art

A conventional adhesive bandage has a pair of opposing adhesively coated plastic strips with a gauze or plastic pad member disposed in the center. The adhesive is a conventional pressure sensitive adhesive. The plastic strip is typically perforated throughout. Adhesive bandages of this type are well known in the art. A common household brand is called "Band-Aid", which is a registered trademark of Johnson and Johnson, Inc., although there are other popular brands.

U.S. Pat. No. 4,117,841 describes a conventional adhesive bandage with certain modifications. The bandage of U.S. Pat. No. 4,117,841 is a self-contained medicated bandage adhesive strip with a rupturable pocket confining a quantity of suitable medicament. It also has a self-contained means for rupturing the pocket.

The bandage of U.S. Pat. No. 4,117,841 does not allow the individual or the physician to select a specific medication for the wound; rather one must use the standard medication that is incorporated into the bandage.

A problem with the conventional adhesive bandage is that, when medication or ointment is placed on the wound, it oozes out on all sides when pressure is applied on the adhesive parts of the strips.

A second problem with conventional adhesive bandages is the thinness of the non-adhesive part of the strip or pad which lies immediately over the wound. Even though there are small perforations, the flow of air is limited and the perforations can collect dust and dirt.

A third problem with the conventional adhesive bandage is that when medication or ointment is used, there is pressure immediately over the wound. This pressure is necessary to confine the medication on the wound. Unfortunately, this pressure impedes the healing process. It restricts the capillary blood flow to the wound as is manifested by the pale colored skin visible upon the removal of the bandage.

DISCLOSURE OF THE INVENTION

The present invention eliminates the above problems. The novel adhesive bandage has a well for receiving medication supplied by the user and for confining the medication to a predetermined area. The well is in the center of a foam block member. the air flow passes through the foam block member, which acts as a dust and dirt filter and also as an aerateor. There are no perforations in the strip so dust and dirt are sealed out.

A flexible flap covers the well which also keeps out dirt and dust. This creates an airspace over the wound which allows air to circulate freely to promote drying and healing. This also eliminates another problem with conventional adhesive bandages. If one wants to inspect the wound, the conventional adhesive bandage is pulled off. This causes discomfort and disturbs the healing process. Moreover, a new bandage would have to be applied for sterility. The flexible flap of the present invention acts as a window for inspecting the wound without replacing the bandage. Another advantage of the present invention is the foam block member which acts as a "doughnut" by exerting light pressure around the wound. This effect causes no pressure on the top of the wound, so as not to impede the capillary blood flow needed in the healing process.

When a wound is stretched by motion or for another reason, this constant irritation disturbs the healing process. By applying an adhesive about the periphery of the foam block member in contact with the skin, a protective environment from frequent stretching of the skin is created. The foam block member is adhesively attached to the skin and to the strip. The non-stretchable portion of the foam block member acts in concert with the strip as a "butterfly". This principle prevents the frequent stretching of the skin and aids the healing process.

The present invention provides an adhesive bandage for confining medication supplied by the user to a predetermined area. The bandage comprises a flexible strip having an adhesive coating on one side; a foam block member with a central aperture adhered to the center of the strip and being of the same width or less than that of the strip; and a flexible flap with an adhesive coating on one side and adhered to the uncoated side of the flexible strip for covering the aperture of the foam block member; and a pair of release sheets for covering the adhesive coating on the flexible strip.

BRIEF DESCRIPTION OF THE DRAWINGS

The above and other objects, features and advantages of the present invention will be more fully apparent to those of ordinary skill in the art to which this invention pertains from the following detailed description, when considered in connection with the accompanying drawings, in which like reference characters designate like or corresponding parts throughout the several views, and wherein.

BEST MODE FOR CARRYING OUT THE INVENTION

Figure 1:
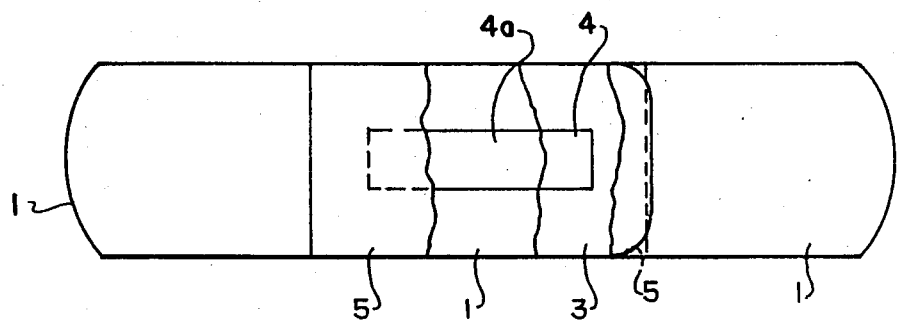
FIG. 1 is a top plan view with parts broken away of a bandage according to the first embodiment of the present invention.
Figure 2:
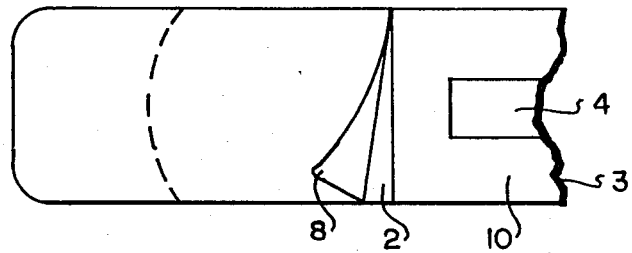
FIG. 2 is a partial bottom plan view of the bandage shown in FIG. 1.
Figure 3:
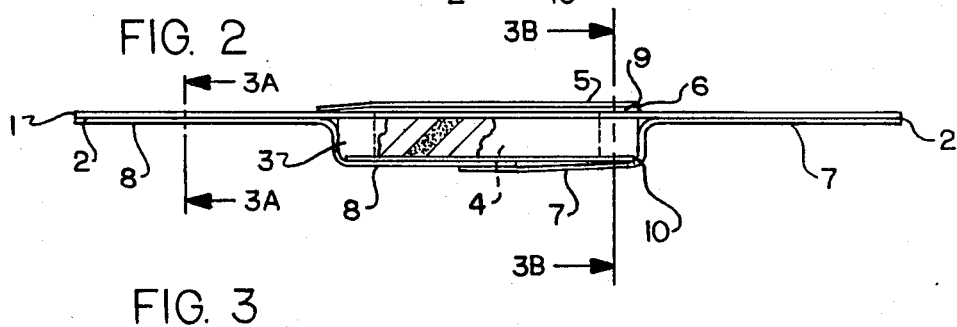
FIG. 3 is a side elevational view of the bandage shown in FIG. 1.
Figure 6:
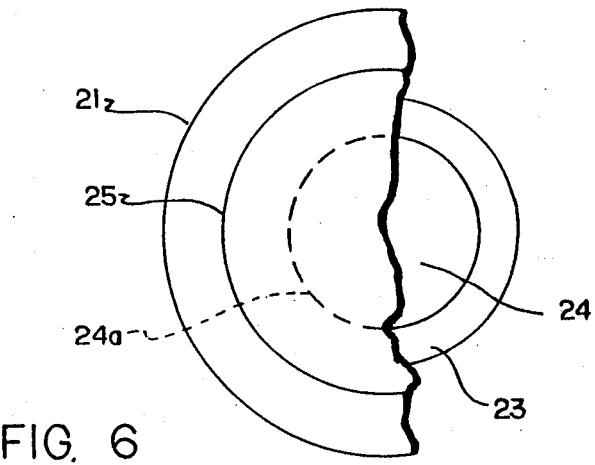
FIG. 6 is a top plan view with parts broken away of a third embodiment of the present invention.

Illustrated in FIGS. 1-3, 3A and 3B is the preferred embodiment of the present invention. In FIGS. 1-3, the bandage of this invention includes a flexible strip 1, which is essentially rectangular and made of plastic. An adhesive coating 2 (shown in FIGS. 3A and 3B) covers one side (the underside as seen in FIG. 3) of the flexible strip 1. The adhesive is a conventional pressure sensitive adhesive. A rectangular foam block member 3 having a central aperture 4 is adhered to the center of the flexible strip 1 through adhesive coating 2. The central aperture 4 extends through the flexible strip 1. Strip 1 has a central aperture 4a in registry with aperture 4. Aperture 4 is the well for receiving medication or ointment supplied by the user.

The foam block member 3 can be as wide as the flexible strip, or it can be less wide. In the preferred embodiment shown, foam block member 3 has the same width as the adhesive coated strip 1, but is shorter. The foam block member 3 may be made from polyurethane foam, foam rubber, gel foam or kany other non-toxic foam material. Foam provides resiliency yet confines the medication to the predetermined area. The resiliency serves to protect the wound from stretching. Also, it exerts a light pressure around the wound rather than directly on the wound.

The foam block member 3 should be at least about one-eighth inch thick to provide enough volume for the medication and to allow air to circulate over the wound.

A flexible flap 5 also made of plastic, covers the aperture 4. An adhesive coating 6 on the underside of the flap 5, as shown in FIG. 3B, adheres a portion of the flap 5 to the uncoated side of the flexible strip 1. A pair of release sheets 7, 8 cover the adhesive coating 2 on the flexible strip 1. A third release sheet 9 can also be used to cover the adhesive coating 6 on the flexible flap 5. The release sheets may be made of plastic or any other suitable material, and may be coated on one side with a conventional release coating, e.g. a silicone.

The preferred embodiment of the invention includes an adhesive coating 10 (FIG. 3B) on the surface of the foam block member 3 that is in contact with the skin. The adhesive coating 10 employed is a material that will partially stick to the skin, similar to adhesive materials currently being sold for foot callouses. This adhesive coating 10 helps seal in the medication by its adhesion to the skin. Furthermore, this adhesion plays an important role in the "butterfly" principle of the bandage. The adhesive coating 10 anchors the foam block member 3 to the skin. The resiliency of the foam block member 3 prevents frequent stretching of the skin. Stretching of a wound disturbs the healing process.

Figure 4:
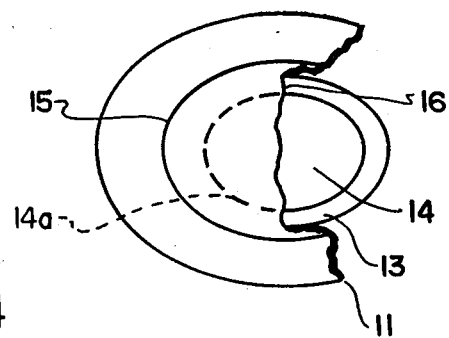
FIG. 4 is a top plan view with parts broken away of a second embodiment of the present invention.
Figure 5:
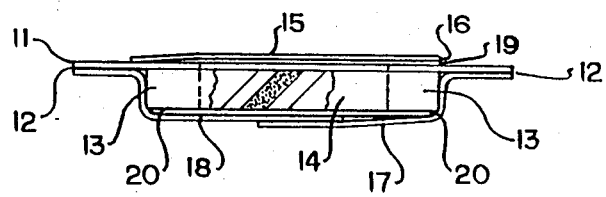
FIG. 5 is a side elevational view of the bandage shown in FIG. 4.

Illustrated in FIGS. 4 and 5 is a second embodiment of the present invention. Since all of the structures have similar purposes and functions as their counter-parts in the preferred embodiment, but differ only in shape, they can be made of the same materials and exhibit the same properties.

A flexible strip 11 of essentially oval shape is made of plastic. An adhesive coating 12 covers one side of the strip 11. An oval foam block member 13 having a central aperture 14 is adhered to the center of the oval strip 11. The flexible strip 11 has a central aperture 14a in registry with aperture 14. The aperture 14 receives medication or ointment supplied by the user.

The foam block member 13 is smaller in diameter along both major and minor areas than the flexible strip 11. It is made from the same materials and is about the same thickness as foam block member 3.

A flexible flap 15, slightly larger than foam block member 13 covers the aperture 14. It is also made of plastic and has an adhesive coating 16 on one side, i.e. on the lower side of flap 15 as shown in FIG. 5. The adhesive coating 16 adheres a portion of the flap 15 to the uncoated side of the flexible strip 11. A pair of release sheets 17, 18 cover the adhesive coating 12 on the strip 11. A third release sheet 19 may also be used to cover the adhesive coating 16 on the flap 15.

An adhesive coating 20 with similar properties as adhesive coating 10 is on the circumference of foam block member 13 which is in contact with the skin.

Illustrated in FIG. 5 is a third embodiment of the present invention. It is a circular bandage. Since all of the structures have similar purposes and functions as their counter-parts in the preferred embodiment, but differ only in shape, they can be made of the same materials and exhibit the same properties.

A circular flexible strip 21 is made of plastic and has an adhesive coating 22 on one side. A circular foam block member 23 having a central aperture 24 is adhered to the center of circular strip 21. The circular flexible strip 21 has a central aperture 24a in registry with aperture 24. This aperture 24 receives medication or ointment supplied by the user.

The foam block member 23 is smaller in diameter than the flexible strip 21. It is made from the same materials and is about the same thickness as foam block member 3.

Figure 7:
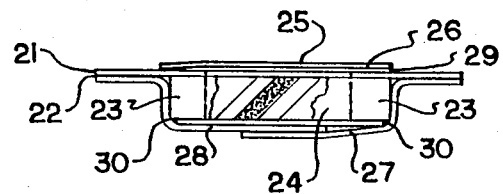
FIG. 7 is a side elevational view of the bandage shown in FIG. 6.

A flexible flap 25 slightly larger than foam block member 23 covers the aperture 24. It is also made of plastic and has an adhesive coating 26 on one side, i.e. on the lower side of flap 25 as shown in FIG. 7. The adhesive coating 26 adheres a portion of the flap 25 to the uncoated side of the circular flexible strip 21. A pair of release sheets 27, 28 cover the adhesive coating 22 on the strip 21. A third release sheet 29 may be used to cover the adhesive coating 26 on the flap 25.

An adhesive coating 30 with similar properties as adhesive coating 10 is on the circumference of foam block member 23 which is in contact with the skin.

Figure 3A:
FIGS. 3A and 3B are cross-sectional views, taken along lines 3A and 3B, respectively, of FIG. 3, with thicknesses exaggerated.
Figure 3B:
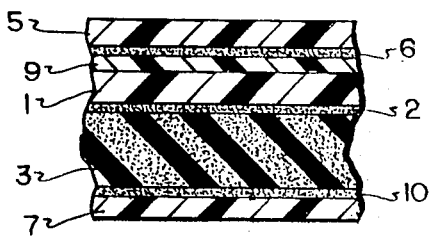

The cross-sectional profiles of bandages according to all three illustrated embodiments of the invention are similar, i.e. as shown in FIGS. 3A and 3B, and so separate cross-sectional views for the second and third embodiments have not been shown.

The bandages of this invention are easy to use. After the first embodiment is explained, the use of the other embodiments will be readily apparent. The user first removes one of the release sheets 7 or 8 and positions the bandage so that the aperture 4 is directly over and around the wound or lesion. Then the user presses the adhesive 2 to the skin. After removing the other release sheet 7 or 8 and pressing the remainder of adhesive 2 to the skin, the user opens the flexible flap 5 and inserts the medication into the well 4. With the removal of the release sheet 9 from the flap 5, the user covers the well confining the medication to the predetermined area.

The medication is preferably in ointment form. Suitable ointments include those containing cortisone or an antibiotic, for example In general, the medication may comprise any therapeutically active agent suitable for topical application, in a pharmaceutically acceptable carrier of paste or cream consistency.

It is important to note as mentioned earlier than the design of this invention facilitates the healing process by not impeding capillary blood flow to the wound. Therefore, for a wound that is bleeding profusely, gauze material may be inserted into the well for an absorbent in lieu of or prior to the addition of medication. The use of medication with the bandage is a choice that may be made at any time during the healing process.

The invention has at least six essential purposes. First, it acts as a "doughnut" by exerting light pressure around the wound with no pressure directly on top of the wound. Thus, the capillary blood flow to the wound is not impeded and the healing process is facilitated. Second, it confines medication or ointment to a predetermined area. Third, the adhesive portion about the periphery of the foam block member helps seal in the medication. Fourth, the stretchable portion of the foam block member prevents frequent stretching of the skin. Fifth, an airspace directly below the flap and over the wound lets air circulate freely to promote drying and healing. Sixth, the flexible flap can also act as a window for checking the condition of the wound without removing the entire bandage.

Since it is apparent that numerous changes and modifications can be made in the above-described details particularly with respect to form or shape of the bandage without departing from the spirit and nature of the invention, it is to be understood that all such changes and modifications are included within the scope of the invention.

What is claimed is:

1. An adhesive bandage comprising:
   (a) a flexible strip having an adhesive coating on one side;
   (b) a generally doughnut shaped foam block member having a central aperture extending therethrough for receiving medication and supplying said medication to a site of the skin requiring medication, said central aperture being open at its top and bottom, said foam block member being adhered to said flexible strip via said adhesive coating, said foam block member being shorter than and not wider than said flexible strip and being positioned on said flexible strip so that both ends of said flexible strip extend beyond said block member;
   (c) said flexible strip having an aperture in registry with the central aperture of said foam block member;
   (d) a flexible flap for covering said aperture of said block member, said flexible flap having an adhesive coating on one side and being adhered via said adhesive coating to the uncoated side of said flexible strip; and
   (e) a pair of release sheets for covering said adhesive coating on said flexible strip.

2. An adhesive bandage as claimed in claim 1, further comprising a third release sheet for covering said adhesive coating on said flexible flap.

3. An adhesive bandage as claimed in claim 1, wherein said foam block member has an adhesive coating about its periphery on the side adapted to be placed against the skin.

4. An adhesive bandage as claimed in claim 3, wherein said adhesive coating is an adhesive material that partially adheres to the skin.

5. An adhesive bandage as claimed in claim 1, wherein said foam block member is at least about $\frac{1}{8}''$ thick.

6. An adhesive bandage as claimed in claim 1, wherein said bandage is essentially rectangular.

7. An adhesive bandage as claimed in claim 1, wherein said bandage is circular.

8. An adhesive bandage as claimed in claim 1, wherein said bandage is circular.

9. An adhesive bandage as claimed in claim 1, wherein said foam block member is resilient.

10. An adhesive bandage as claimed in claim 1, wherein said foam block member is of essentially uniform thickness.

* * * * *